United States Patent [19]

Drabek et al.

[11] 3,934,010
[45] Jan. 20, 1976

[54] INSECTICIDAL COMPOSITION AND METHOD UTILIZING PHOSPHORIC ACID PHENYLSULPHONAMIDE ESTERS

[75] Inventors: Jozef Drabek, Allschwil; Denis Varsanyi, Arlesheim, both of Switzerland

[73] Assignee: Ciba-Geigy Corporation, Ardsley, N.Y.

[22] Filed: Sept. 23, 1974

[21] Appl. No.: 508,592

Related U.S. Application Data

[62] Division of Ser. No. 310,507, Nov. 29, 1972, Pat. No. 3,855,362.

[30] Foreign Application Priority Data

Dec. 3, 1971 Switzerland.................... 17619/71
Sept. 22, 1972 Switzerland.................... 13869/72

[52] U.S. Cl............................. 424/211; 424/DIG. 8
[51] Int. Cl.²........................................... A01N 9/36
[58] Field of Search........ 424/211, DIG. 8; 260/944

[56] References Cited
UNITED STATES PATENTS

3,309,371    3/1967    Curry et al..................... 260/944 X

OTHER PUBLICATIONS

Wagner et al., *J. Med. Chem.* 8(3), 1965, pp. 377 to 383.

*Primary Examiner*—Albert T. Meyers
*Assistant Examiner*—Allen J. Robinson
*Attorney, Agent, or Firm*—Harry Falber

[57] ABSTRACT

Insecticidal and acaricidal compositions and methods for combating insects and acaricides are provided wherein the active insecticidal ingredients are phosphoric acid phenylsulphonamide esters of the formula

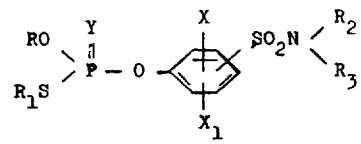

wherein Y represents oxygen or sulphur, R represents alkyl with 1 to 5 carbon atoms, $R_1$ represents alkyl with 1 to 5 carbon atoms, alkenyl and alkinyl each with 3 to 5 carbon atoms, alkoxyalkyl with 1 to 5 carbon atoms in each of the moieties, alkylthioalkyl with 1 to 5 carbon atoms in each of the moieties, or haloalkyl with 1 to 5 carbon atoms, $R_2$ represents hydrogen, alkyl with 1 to 5 carbon atoms or alkenyl with 3 to 5 carbon atoms, $R_3$ represents hydrogen and X and $X_1$ each represents halogen or alkyl with 1 to 5 carbon atoms, or $R_3$ represents alkyl with 1 to 5 carbon atoms and X and $X_1$ each represents hydrogen, halogen or alkyl with 1 to 5 carbon atoms.

8 Claims, No Drawings

INSECTICIDAL COMPOSITION AND METHOD UTILIZING PHOSPHORIC ACID PHENYLSULPHONAMIDE ESTERS

This is a divisional of application Ser. No. 310,507 filed Nov. 29, 1972, now U.S. Pat. No. 3,855,362.

The present invention relates to phosphoric acid phenylsulphonamide esters, a process for their manufacture and their use in pest control.

The compounds have the formula

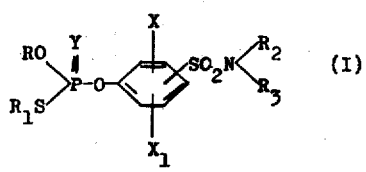

wherein Y represents oxygen or sulphur, R represents alkyl with 1 to 5 carbon atoms, $R_1$ represents alkyl with 1 to 5 carbon atoms, alkenyl and alkinyl each with 3 to 5 carbon atoms, alkoxyalkyl with 1 to 5 carbon atoms in each of the moieties, alkylthioalkyl with 1 to 5 carbon atoms in each of the moieties, or haloalkyl with 1 to 5 carbon atoms, $R_2$ represents hydrogen, alkyl with 1 to 5 carbon atoms or alkenyl with 3 to 5 carbon atoms, $R_3$ represents hydrogen and X and $X_1$ each represents halogen or alkyl with 1 to 5 carbon atoms, or $R_3$ represents alkyl with 1 to 5 carbon atoms and X and $X_1$ each represents hydrogen, halogen or alkyl with 1 to 5 carbon atoms.

Halogen is to be understood as meaning fluorine, chlorine, bromine or iodine, but in particular chlorine. Preferred haloalkyl groups with 1 to 5 carbon atoms are $Cl-CH_2-CH_2-$, $Cl_3C-$ and $F_3C-$.

The groups cited hereinabove which are possible for R to $R_3$, X and $X_1$, may be straight-chain or branched. Examples of such groups include: methyl, methoxy, methoxymethyl, ethyl, ethoxyethyl, ethylthioethyl, propyl, isopropyl, n-, i-, sec. and tert.butyl, n-pentyl and the isomers thereof, allyl, methallyl, n-penten-5-yl, propargyl, isobutinyl.

Preferred compounds on account of their action are those of the formula I, wherein R represents methyl or ethyl, $R_1$ represents propyl, n-butyl, n-pentyl or $C_2H_5OCH_2CH_2-$, $R_2$ represents hydrogen, methyl or ethyl, $R_3$ represents methyl or ethyl, X and $X_1$ each represents hydrogen or chlorine, and Y represents oxygen or sulphur.

Particularly preferred compounds, however, are those of the formula I, wherein R represents ethyl, $R_1$ represents propyl, n-butyl, $C_2H_5OCH_2CH_2-$ or n-amyl, $R_2$ and $R_3$ each represents methyl or ethyl, X and $X_1$ represent hydrogen or chlorine and Y represents oxygen.

The compounds of the formula I can be manufactured according to methods which are known per se:

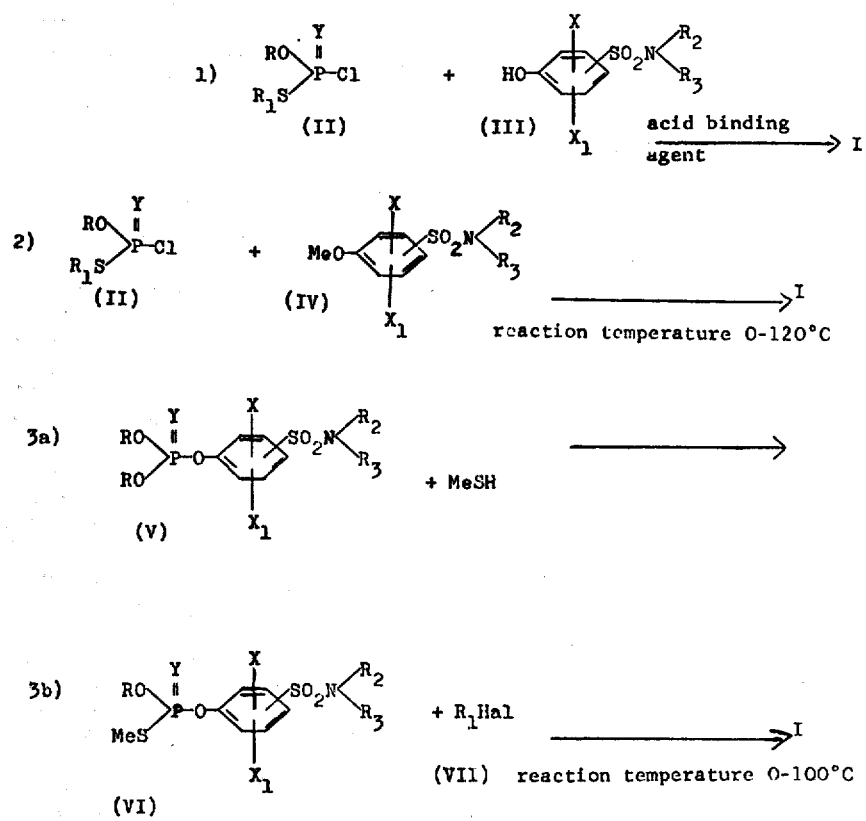

In the formulae II to VII, R to $R_3$, X, $X_1$ and A have the meanings given in respect of the formula I, Me represents an alkali metal, in particular sodium or potassium, ammonium or alkylammonium with up to 5 carbon atoms, and Hal represents chlorine or bromine.

Suitable acid binding agents are: tertiary amines, e.g. trialkylamines, pyridine, dialkylanilines; inorganic bases, such as hydroxides; carbonates and bicarbonates of alkali and alkaline earth metals. It is sometimes necessary to use catalysts in the reactions, e.g. copper or copper chloride.

Processes 1, 2, 3a and 3b may be carried out at normal pressure (3a at up to 10 atmospheres absolute pressure) and in solvents or diluents. Suitable solvents or diluents are e.g. ethers and ethereal compounds, such as diethyl ether, dipropyl ether, dioxan, dimethoxyethane, tetrahydrofuran; amides, such as N,N-dialkylated carboxylic amides; aliphatic, aromatic and halogenated hydrocarbons, in particular benzene, toluene, xylenes, chloroform, chlorobenzene; nitriles, such as acetonitrile; dimethyl sulphoxide, ketones such as acetone, methyl ethyl ketone.

Some of the starting materials of the formulae II and V are known compounds which can be manufactured in analogous manner by known methods. The compounds of the formula I display a broad biocidal activity and are therefore suitable for combating various plant and animal pests and as plant growth regulators. Surprisingly, however, the compounds of the formula possess insecticidal and acaricidalt properties which are superior to those of known, analogous compounds, and they may be used against all development stages, e.g. eggs, larvae, pupae, nymphs and addults, of insects and representatives of the order Acarina, for example against insects of the families:

| | |
|---|---|
| Tettigonidae | Tenebrionidae |
| Gryllidae | Chrysomelidae |
| Gryllotalpidae | Bruchidae |
| Blattidae | Tineidae |
| Reduviidae | Noctindae |
| Phyrrhocoriae | Lymatriidae |
| Cimicidae | Pyralidae |
| Delphacidae | Culicidae |
| Aphididae | Tipulidae |
| Diaspididae | Stomoxydae |
| Pseudococcidae | Trypetidae |
| Scarabacidae | Muscidae |
| Dermestidae | Calliphoridae and |
| Coccinellidae | Pulicidae |

Acarida of the families:
Ixodidae
Argasidae
Tetranychidae and
Dermanyssidae.

The insecticidal or acaricidal action can be substantially broadened and adapted to the particular circumstances by the addition of other insecticides and/or acaracides.

Suitable additives include, for example, the following active substances:
Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-0,2,4,5-trichlorophenylthiophosphate (RONNEL)
O-ethyl-0,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert. butyl-2-chlorophenyl-N-methyl-O-methylamidophosphate (CRUFOMATE)
O,O-dimethyl-O-(3-methyl-4-methylmercaptophenyl) thiophosphate (FENTHION)
Isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)phosphate
2-chloro-1-(2,4-dichlorophenyl)vinyl-diethylphosphate (CHLOROFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran -7-yl)-thiophosphate (COUMAPHOS)
2,3-p-dioxandithiol-S,S-bis(O,O-diethyldithiophosphate) (DIOXATHION)
5-[(6-chloro-2-oxo-3benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol -5- (4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)

O,O-diethyl-O-(2-isopropyl-4-methyl-6-pyrimidyl)-thiophosphate (DIAZINON)
O,O-diethyl-O-(2-chinoxalyl)thiophosphate
O,O-dimethyl-S-(4-oxo-1,2,3-benzotriazin-3(4H)-ylmethyl)-dithiophosphate (AZINPHOS-METHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O( or S)-2-(ethylthioethyl)thiophosphate (DEMETON-S-METHYL)
2-(O,O-dimethyll-phosphoryl-thiomethyl)-5-methoxy-pyron-4-3,4-dichlorobenzyl-triphenyl-phosphoniumchloride
O,O-diethyl-S-(2,5-dichlorophenylthiomethyl(dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramido (VAMIDOTHION)
O,O-diethyl-O-[2-dimethylamine-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bomophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-diemthyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHIOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHIOATE)
O,O-diethyl-S-(carbofluorethoxy-phenylmethyl)-dithiophosphate
O,O-dimethyl-S-carboisopropoxy-phenylmethyl-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl) thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULPOTON)
Bis-O,O-diethylthiophosphoric acid anhydride (SULFOTEP)
Dimethyl-1,3di(carbomethoxy)-1-propen-2-yl-phosphate
Dimethyl-(2,2,2-trichloro-1-butyroyloxyethyl)phosphate (BUTONATE)
O,O-dimethyl-O-(2,2-dichloro-1-methoxy-vinyl)-phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethyoxyvinyl)phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)d sulphide
2-methoxy-4H-1,3,2,benzodioxaphosphorin-2-oxide
Octamethylpyrophosphoramide (SCHRADAN)
Bis (dimethoxythiospphinylsulphido)-phenylmethane
N,N,N',N'-tetramethyldiamidofluorophosphate (DIMEFOX)
O-phenyl-O-p-nitrophenyl-methanthiophosphonate (COLEP)

O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7-phosphate
S-(1-phthalimidoethyl)-O,O-diethyldithiophosphate
O,O-dimethyl-O-(3-chloro-4-diethylsulphamyl-phenyl)-thiophosphate
O-methyl-O-(2-carbisopropoxyphenyl)-amidothiophosphate
5-(O,O-dimethylphosphoryl)-6-chloro-bicyclo(3.2.0)-heptadiene
O-methyl-O-(2-i-propoxycarbonyl-1-methylvinyl)-ethylamidophosphate.

NITROPHENOLS AND DERIVATIVES 4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

MISCELLANEOUS pyrethin I
pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-quinoxaline (Quinomethionate)
(1)-3-(2-furfuryl)-2-methyl-4-oxocyclopent-2-enyl-(1)-(cis+-trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorobenzylsulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside] 2-thio-1,3-dithiolo-(,5-6)-quinoxaline [Thiochinox]
prop-2-ynyl-(4-t-butylphenoxy)-cyclohexylsulphite [Propargil].

FORMAMIDES 1-dimethyl-2-(2'methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imine)-pyrolidine.

UREA

N-2-methyl-4-chlorophenyl-N',N'-dimethyl-thiourea.

CARBAMATE 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-0-)methylcarbamoyl)-oxime
1-(dimethylcarbamoyl)-5-methyl-3-pyrazoyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-chinadyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)

2-(2-propinloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3-dimethylamino-methyleneiminophenyl-N-methylcarbamate (FORMETANATE) and their salts
1-methylthio-ehtylimino-N-methylcarbamate (METHOMYL)
2-methylcarbamoyloximino-1,3-dithiolane
5-methyl-2-methylcarbomoyloximino-1,3-oxythiolane
2-(1-methoxy-2-propoxy)phenyl-N-methylcarbamate
2(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithioland-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetyl-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-γ-chloroallylamino)-3,5xylyl-N-methyl-carbamate
4-(methyl-β-chloroallylamino)-3,5-xylyl-N-methyl-carbamate
1-(β-ethoxycarbonalethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methyl carbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate

CHLORINATED HYDROCARBONS

γ-hexachlorocyclohexane [GAMMEXANE; LINDAN; γ HCH]
1,2,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α5,6,7,8-,8α-oxtahydro-exo-1,4-endo-5,8-dimethanonaphthalene [DIFLORIN]
1,2,3,4,10,10-hexachloro-5,7-epoxy-1,4,4α,5,6,7,8-,8α-octyhydro-endo-endo-5,8-dimethanonaphthalene [ENDRIN]

The active substances of the formula I are also suitable for combating representatives of the division Thallophyta, e.g. viruses, bacteria and fungi. They thus possess fungicidal properties against phytophathogenic fungi on various cultivated plants, such as cereals, maize, rice, vegetables, ornamental plants, fruit trees, vines, farm products, etc.

With the new active substances it is possible to control or destroy fungi occuring on fruit, blossom, leaves stems, tubers and roots, and from which parts of plants which grow later then also remain free. The active substances of the formula I are active in particular against phytopahtogenic fungi belonging to the following classes:

Oomycetes, Zygomycetes, Ascomycetes, Basidiomycetes, Denteromycetes.

In addition, the new active substances can also be used for treating seeds, fruit, tubers etc., and the protecting them from fungus infections, for example from smut fungi of all kinds, such as Ustilaginales, e.g., Ustilago, Tilletia, Urocystis, Turbucinia and Phoma types.

In addition to the above cited acaricides and insecticides, it is also possible to admix the active substances of the formula I with, for example, bactericides, fungistatic agents, bacteriostatic agents, nematocides and/or e.g. the following fungicides, in order to broaden the activity spectrum:

dodecylquanidine acetate (DODINE)
pentachloronitrobenzene (QUINTOZENE)
pentachlorophenol (PCP)

2-(1-methyl-n-propyl)-4,6-dinitrophenyl -2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenylsulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramidisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxy-pyrimidine
methyl-N-benzimidazole-2-yl-N-(butylcarbamoyl)-carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine pentachlorobenzyl alcohol.

Furthermore, the compounds of the formula I are suitable for combating plant pathogenic nematodes.

The compounds of the formula I may be used as pure active substance or together with suitable carriers and-/or additives. Suitable carriers and additives can be solid or liquid and correspond to the substance conventionally used in formulation technique such, for example, as solvents dispersants, wetting agents, adhesives, thickeners, binders and/ or fertilisers.

For application, the compounds of the formula I may be processed to dusts, emulsion concentrates, granules, dispersions, sprays, to solutions, or suspensions in the conventional formulation which is commonly employed in application technology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms: Solid forms:

Dusts, tracking agents, granules, coated granules, impregnated granules and homogeneous granules.
Liquid forms: a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesuim oxide, ground synthetic materials, fertilisers, for example ammonium sulphate, ammonium phosphate, ammonium nitrate, urea, ground vegetable products, such as corn meal, bark dust, sawdust, nutshell means, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form g/liter microgranules having a bulk denisty of 300 g/litre to 600 g/liter can also be manufactured with the aid of atomisers. The dusting can be carried out from aircraft over extensive areas of cultures of useful plants.

It is also possible to obtain granules by compacting the carrier with the active substance and carrier and subsequently comminuting the product.

To these mixtures can also be added additives which stabilize the active substances and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein-chalk mixture, cellulose derivates (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, optionally additives which stablize the active substance, surface-active substance and antifoam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation of naphthalene or naphthalene sulfonic acids with phenol and formaldehyde, as well as alkali, ammonium and alkaline earth metal salts of sulfonic acid, in addition, alkyaryl sulfonates, alkali and alkaline earth metals salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with additives cited hereinabove in such a manner that, in wettable powders, the solid particle size of from 0.02 to 0.04 and in pastes, of 0.03 is not exceeded. To produce emulsifiable concentrates and pastes, dispersing agents such as those cited above, organic solvents and water are used. Examples of suitable solvents are: alcohols, benzene, xylene, toluene, dimethyl sulfoxide, and mineral oil fractions boiling between 120° and 350°C. The solvents must be practically odourless, not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

DUSTS

The following substances are used to manufacture (a) a 5% and (b) a 2% dust:
a. 5 parts of active substance 95 parts of talcum
b. 2 parts of active substance 1 part of highly disperse silica 97 parts of talcum.

The active substances are mixed with the carriers and ground.

GRANULES

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

WETTABLE POWDER

The following constituents are used for the preparation of (a) a 40%, (b) and (c) a 25%, and (d) a 10% wettable powder:
a. 40 parts of active substance, 5 parts of sodium lignin sulphonate, 1 part of sodium dibutyl-naphthalene sulphonate, 54 parts of silica acid.
b. 25 parts of active substance, 4.5 parts of calcium lignin sulphonate 1.9 parts of Champagne chalk/hydroxyethyl cellulose mixture (1:1), 1.5 parts of sodium dibutyl naphthalene sulphonate, 19.5 parts of silica acid, 19.5 parts of Champagne chalk, 28.1 parts of kaolin.
c. 25 parts of active substance, 2.5 parts of isooctylphenoxy-polyoxyethylene-ethanol, 1.7 parts of Champagne chalk/hydroxyethyl cellulose mixture (1:1), 8.3 parts of sodium aluminium silicate,
16.5 parts of kieselguhr, 46 parts of kaolin.
d. 10 parts of active substance, 3 parts of a mixture of the sodium salts of saturated fatty alcohol sulphates, 5 parts of naphthalenesulphonic acid/formaldehyde condensate, 82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

EMULSIFIABLE CONCENTRATES

The following substances are used to produce (a) a 10% and (b) a 25% emulsifiable concentate:
a. 10 parts of active substance, 3.4 parts of epoxidised vegetable oil, 13.4 parts of a combination emulsifier consisting of fatty alcohol polyglycol ether and alkylarylsulphonate calcium salt, 40 parts of dimethylformamide, 43.2 parts of xylene.
b. 25 parts of active substance, 2.5 parts of epoxidised vegetable oil, 10 parts of an alkylarylsulphonate/fatty alcoholpolyglycol ether mixture 5 parts of dimethylformamide, 57.5 parts of xylene.

From these concentrates it is possible to produce, by dilution with water, emulsion of any desired concentration.

SPRAY

The following constituents are used to prepare a 5% spray:

5 parts of active substance,
1 part of epichlorohydrin,
94 parts of benzine (boiling limits 160°-190°C).

EXAMPLE 1

Manufacture of O-ethyl-S-propyl-O-(4'-N,N-dimethylsulphonamidophenyl)-thiol-phosphoric acid ester To a suspension of 14.4 g of 4-N,N-dimethylsulphonamidophenol in 110 ml of benzene are added 7.2 g of triethylamine. While stirring constantly, 14.5 g of O-ethyl-S-n-propylchlorothiophosphate are added dropwise. The mixture is stirred for 12 hours at room temperature, when washed with water, 3% sodium carbonate solution and again with water, and dried over anhydrous sodium sulphate.

The benzene is distilled off and the residue purified by means of molecular distillation (135°C/0,001 Torr) to give the compound of the formula

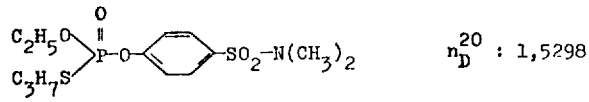

$n_D^{20}$ : 1,5298

The following compounds are also manufactured in analogous manner:

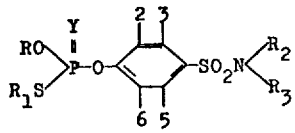

| R | R₁ | R₂ | R₃ | Y | 2 | 3 | 5 | 6 | |
|---|---|---|---|---|---|---|---|---|---|
| C₂H₅- | (n)C₄H₉- | CH₃- | CH₃- | O | H | H | H | H | $n_D^{20}$ = 1,5268 |
| C₂H₅- | C₂H₅OCH₂CH₂- | CH₃- | CH₃- | O | H | H | H | H | $n_D^{20}$ = 1,5335 |
| C₂H₅- | (n)C₃H₇- | CH₃- | CH₃- | O | Cl | H | H | H | $n_D^{20}$ = 1,5378 |
| C₂H₅- | (n)C₃H₇- | C₂H₅- | C₂H₅- | O | H | H | H | H | $n_D^{20}$ = 1,5238 |
| C₂H₅- | (n)C₃H₇- | CH₃- | CH₃- | S | Cl | H | H | H | $n_D^{20}$ = 1,5593 |
| C₂H₅- | (n)C₃H₇- | C₂H₅- | C₂H₅- | S | H | H | H | H | Smp.: 64°C |
| C₂H₅- | (n)C₃H₇- | CH₃- | CH₃- | S | H | H | H | H | $n_D^{20}$ = 1,5514 |
| C₂H₅- | (n)C₃H₇- | CH₃- | CH₃- | S | Cl | H | Cl | H | $n_D^{20}$ = 1,5710 |
| C₂H₅- | (n)C₅H₁₁- | CH₃- | CH₃- | S | H | H | H | H | $n_D^{20}$ = 1,5393 |
| C₂H₅- | (n)C₃H₇- | CH₃- | CH₃- | O | H | Cl | H | H | $n_D^{20}$ = 1,5390 |
| C₂H₅- | (n)C₃H₇- | CH₃- | CH₃- | O | Cl | H | Cl | H | $n_D^{25}$ = 1,5381 |
| C₂H₅- | (n)C₃H₇- | CH₃- | CH₃- | O | CH₃ | H | H | H | |
| C₂H₅- | (n)C₃H₇- | CH₃- | CH₃- | O | H | CH₃ | H | H | |
| C₂H₅- | (n)C₃H₇- | H | CH₃- | O | H | H | H | H | |
| C₂H₅- | (n)C₃H₇- | H | H | O | Cl | H | H | H | |

EXAMPLE 2

A. Insecticidal Ingest Poison Action

Tobacco and potato plants are sprayed with a 0.05% aqueous emulsion (obtained from a 10% emulsifiable concentrate).

After the coating has dried, Egyptian cotton leaf worms (*Spodoptera literalis*) are settled on the tobacco plants and Colarado potato beetle larvae (*Leptinotarsa decemlineata*) on the potato plants. The test is carried out at 24°C and 60% relative humidity. In the above test, the compounds according to Example 1 display ingest poison action against Spodoptera litoratis and Leptinotarsa decemlineata.

B. Systemic Insecticidal Action

To determine the systemic action, rooted bean plants (Vicia fabae) are put into a 0.01% aqueous active substance solution (obtained from a 10% emulsifiable concentrate). After 24 hours, aphids (Aphis fabae) are placed on the parts of the plant above the soil. The aphids are protected from contact and gas action by means of a special device. The test is carried out at 24°C and 70% relative humidity. In the above tests the compounds according to Example I displayed good insecticidal ingest poison action and systemic insecticidal action.

EXAMPLE 3

Action Against *Chilo Suppressalis*

Six rice plants at a time of the variety Caloro were transplanted into plastic pots (diameter at the top = 17 cm) and reared to a height of about 60 cm. Infestation with *Chilo suppressalis* larvae (L₁: 3–4 mm long) took place 2 days after application of the active substance in granule form to the paddy water (rate of application: 8 kg of active substance per hectare). Evaluation of the insecticidal action took place 10 days after application of the granules.

The compounds according to Example I were active in the above test against *Chilo suppressalis*.

EXAMPLE 4

Action Against Soil Insects

Sterilised compost earth was homogeneously mixed with a wettable powder containing 25% of active substance so that there resulted a rate of application of 8 kg of active substance per hectare.

Young zucchetti plants (*Cucumis pepo*) were put into plastic pots with the treated soil (3 plants per pot; diameter of pot = 7 cm). Each pot was infected immediately afterwards with 5 *Aulacophora femoralis* and Pachmoda or Chortiphila larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against *Aulacophora fermoralis*, Pachmoda and chlortophila larvae.

EXAMPLE 5

Action Against Ticks

A. Rhicephalus bursa

In each of two test series 5 adult ticks and 50 tick larvae are counted into a glass tube and immersed for 1 to 2 minutes in 2 ml of an aqueous emulsion from an amulsion series each containing 100, 10, 1 and 0.1 ppm of test substance. The tube is then sealed with a standardised cotton wool plug and placed on its head, so that the active substance emulsion can be adsorbed by the cotton wool.

In the case of the adults evaluation takes place after 2 weeks, and in that of the larvae after 2 days. Each test is repeated twice.

The compounds according to Example 1 act in the above test against adults and larvae of Rhicephalus bursa.

B. Boophilus microplus (larvae)

Tests are carried out in each case with 20 OP-sensitive larvae using an analogous dilution series as in the case of test A. (The resistance relates to the tolerability of Diazinon).

The compounds according to Example 1 act in these tests against sensitive and OR resistant larvae of Boophilus microplus.

EXAMPLE 6

Acaracidal Action

*Phaseolus vulgaris* (dwarf beans) have an infested piece of leaf from a mass culture of *Tetranychus urticae* placed on them 12 hours before the test for the acaricidal action. The mobile stages which have passed over are sprayed with the emulsified test preparations from a chromatography atomiser so that the spray broth does not run off. The number of living and dead larvae, adults and eggs are evaluated after 7 days under a stereoscopic microscope and the result expressed in percentages. During the "interim", the treated plants are kept in greenhouse compartments at 25°C.

The compounds according to Example 1 are active in the above test against eggs, larvae and adults of *Tetranchus urticae*.

EXAMPLE 7

Action Against Soil Nematodes

To test the action against soil nematodes, the active substance (in a concentration of 50 ppm) is applied to and intimately mixed with soil infected with root gall nematodes (*Meloidgyne Avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing. The compounds according to Example display good action against *Meloidgyne Avenaria*.

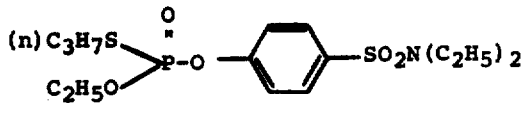

We claim:

1. An insecticidal and acaricidal composition comprising an insecticidally and acaricidally effective amount of a compound of the formula

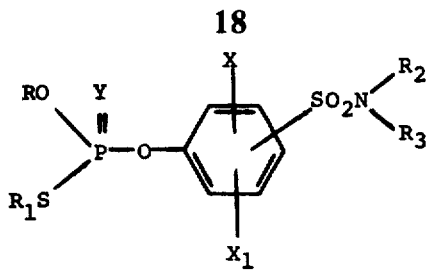

wherein R represents methyl or ethyl, $R_1$ represents propyl, n-butyl, n-pentyl or $C_2H_5OCH_2CH_2$—, $R_2$ represents hydrogen, methyl or ethyl, $R_3$ represents methyl or ethyl, X and $X_1$ each represents hydrogen or chlorine, and Y represents oxygen or sulphur, together with a suitable carrier therefor.

2. The composition of claim 1, wherein R represents ethyl, $R_1$ represents propyl, n-butyl, $C_2H_5OCH_2CH_2$- or n-amyl, $R_2$ and $R_3$ each represents methyl or ethyl, X and $X_1$ represent hydrogen or chlorine and Y represents oxygen.

3. The composition of claim 2, wherein said compound is

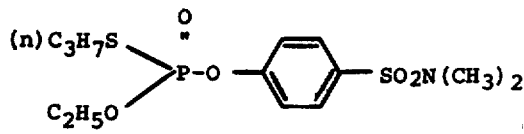

4. The composition of claim 2, wherein said compound is

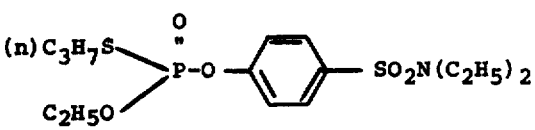

5. A method for combatting insects and acaricides which comprises applying to the loci thereof an insecticidally and acaricidally effective amount of a compound according to the formula of claim 1.

6. The method of claim 5, wherein R represents ethyl, $R_1$ represents propyl, n-butyl, $C_2H_5OCH_2CH_2$— or n-amyl, $R_2$ and $R_3$ each represents methyl or ethyl, X and $X_1$ represent hydrogen or chlorine and Y represents oxygen.

7. The method of claim 6, wherein said compound is

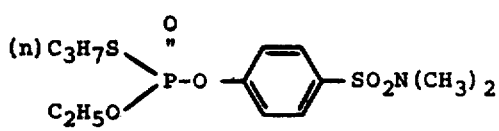

8. The method of claim 6, wherein said compound is